United States Patent [19]

Fisher

[11] Patent Number: 5,514,084

[45] Date of Patent: May 7, 1996

[54] RETRACTABLE WIPE FOR CLEANING ENDOSCOPIC SURGICAL DEVICES

[76] Inventor: Yale Fisher, 34 E. 72nd St., Apt. #5N, New York, N.Y. 10021

[21] Appl. No.: 280,372

[22] Filed: Jul. 26, 1994

[51] Int. Cl.⁶ .................................................. A61M 35/00
[52] U.S. Cl. .................. 604/1; 600/157; 604/15; 604/267
[58] Field of Search ............... 128/4; 604/1, 15, 604/16, 266, 267; 606/127, 162; 15/244.1, 104.03, 104.04; 600/157

[56] References Cited

U.S. PATENT DOCUMENTS

| | | | |
|---|---|---|---|
| 2,545,091 | 3/1951 | Livermore | 15/184 |
| 3,935,863 | 2/1976 | Kliger | 604/267 X |
| 4,227,278 | 10/1980 | Rakin et al. | 15/234 |
| 4,281,646 | 8/1981 | Kinoshita | 128/6 |
| 4,919,113 | 4/1990 | Sakamoto et al. | 128/4 |
| 5,188,630 | 2/1993 | Christoudias | 604/1 X |
| 5,203,767 | 4/1993 | Cloyd | 604/15 X |
| 5,274,874 | 1/1994 | Cercone et al. | 15/244.1 |
| 5,284,128 | 2/1994 | Hart | 128/4 |
| 5,295,952 | 3/1994 | Pietrafitta | 604/1 |
| 5,308,316 | 5/1994 | Williams et al. | 604/13 |
| 5,337,730 | 8/1994 | Maguire | 128/4 |
| 5,375,589 | 12/1994 | Bhatta | 604/267 X |
| 5,382,297 | 1/1995 | Valentine et al. | 15/244.1 X |
| 5,392,766 | 2/1995 | Masterson et al. | 128/4 |

FOREIGN PATENT DOCUMENTS

| | | | |
|---|---|---|---|
| 5103751 | 5/1993 | Japan | 128/4 |

Primary Examiner—Richard J. Apley
Assistant Examiner—Beverly M. Flanagan
Attorney, Agent, or Firm—Abelman, Frayne & Schwab

[57] ABSTRACT

A retractable wipe is disclosed for cleaning the lens at the forward end of an endoscope while it is inside the body cavity during endoscopic surgery and a method for using the retractable wipe in such a capacity. The retractable wipe allows for the wiping element of a wiping device to be in a protected, retracted position during entry into the surgical area and then provides for the wiping element to be extended for use once inside the surgical area. While the invention is useful in several types of endoscopic surgery. It is especially useful in ophthalmic surgery. The device may be made in various sizes, so that it will fit in the small incisions used in ophthaimic surgery. The invention is also especially useful in laparoscopic surgery. Due to the abundance of fat and other bodily materials in the abdominal area, which tend to foul the endoscope and frequent endoscope cleaning is required to maintain a clear view of the surgical view.

16 Claims, 3 Drawing Sheets

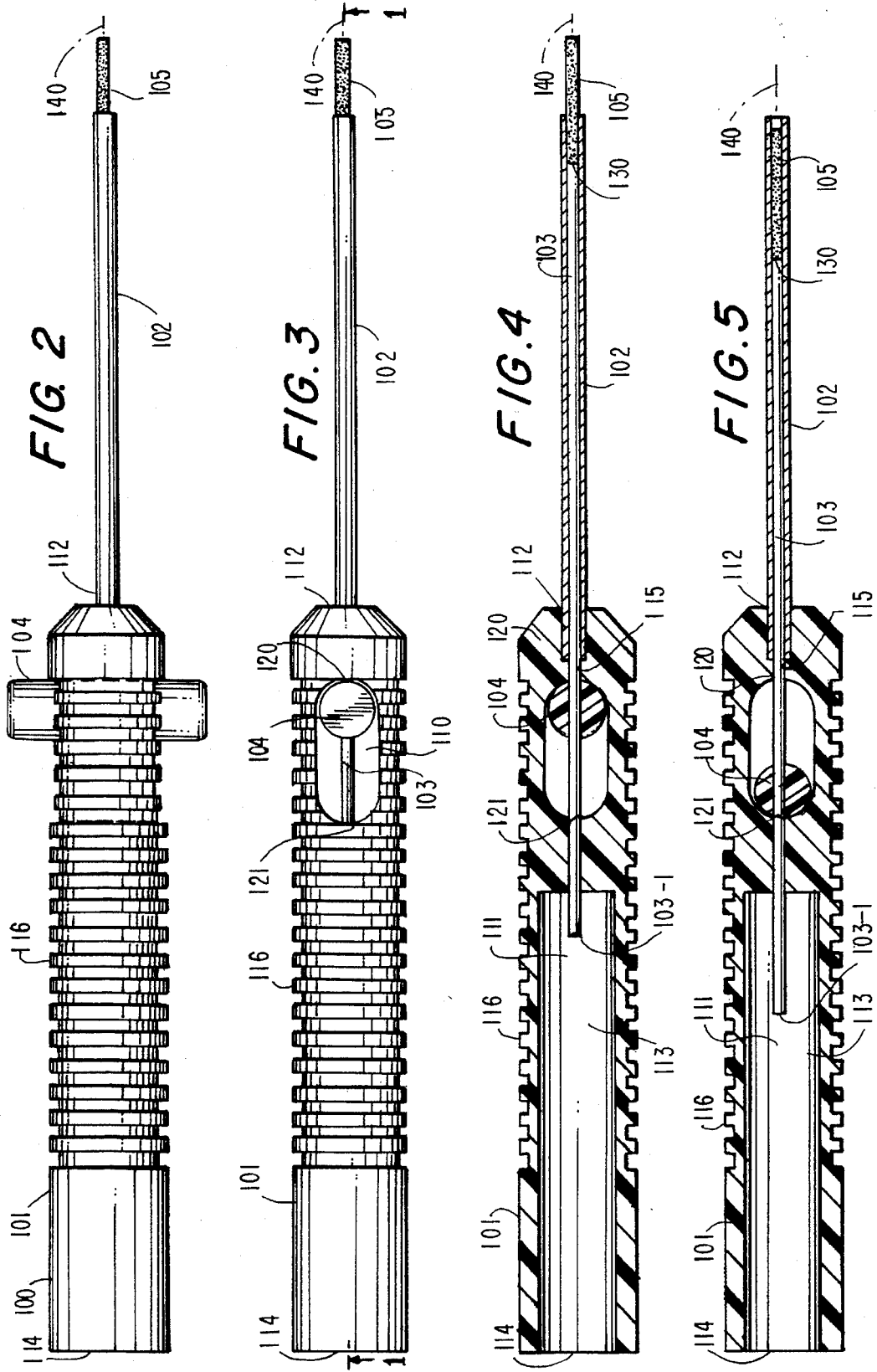

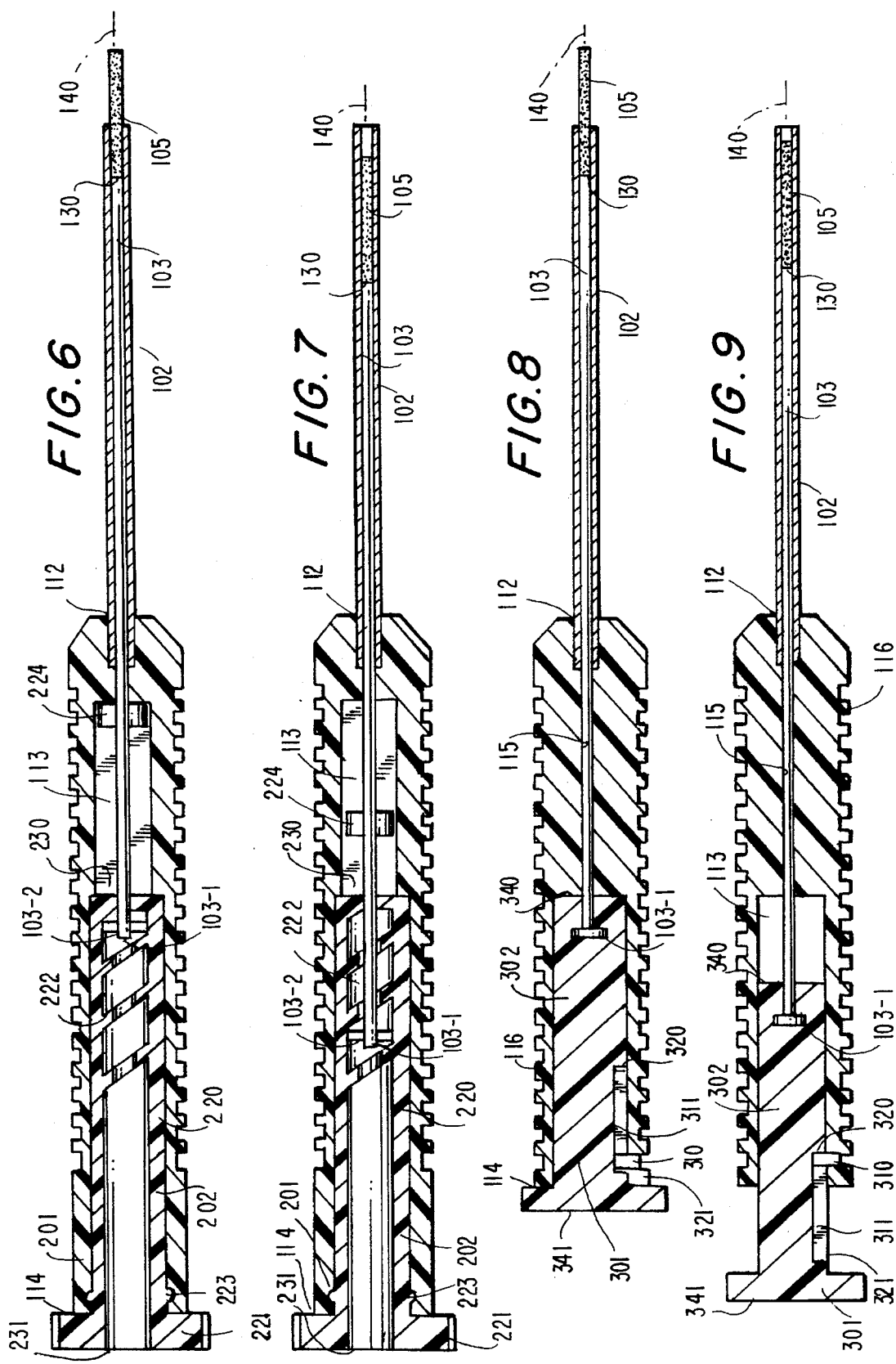

RETRACTABLE WIPE FOR CLEANING ENDOSCOPIC SURGICAL DEVICES

FIELD OF THE INVENTION

This invention relates to endoscopic surgery and more particularly to a retractable wiping device for the tip of an endoscope for maintaining a clean, clear field of vision through the endoscope during the surgical procedure. The invention is useful in all types of endoscopic surgery and especially in ophthalmic surgery. The retractable wiping device may be made in various sizes, including very small, so that it will fit in the very small incisions used in ophthalmic surgery. The invention is also quite useful in laparoscopic surgery. Due to the abundance of fat and other bodily materials in the abdominal area, which tend to foul the endoscope, frequent endoscope cleaning is required to maintain a clear view of the surgical area.

BACKGROUND OF THE INVENTION

Endoscopic surgery may be accomplished in multiple ways. At least one incision is made or a body orifice is utilized to permit an endoscope with visualization optics to enter into the body cavity and be positioned adjacent the surgical field of interest. The working ends of surgical implements may be inserted into this incision or may be attached to the endoscope. Alternately, more than one incision into the body cavity may be made. One incision permits the independent placement of an endoscope in the body cavity. Other incisions permit the separate emplacement of the working ends of various surgical implements.

During both a) entry into an incision in the body, and b) during the course of the surgical procedure, moisture or body materials may be present at the tip of the endoscope, which would blur the surgeon's vision of the surgical field. Hence, the tip must be cleaned of such material.

It is presently known to clean the lens at the tip of the endoscope by squirting an endoscope with water or some other liquid. Such devices are typically shown in U.S. Pat. Nos. 4,281,646, 4,919,113, and Japanese Patent 5-103751. However, under certain surgical procedures, particularly in which the field is pressurized with a gas such as air, it is undesirable to introduce such additional moisture into the surgical field. Further, spraying liquid on the endoscope may not provide thorough cleaning and may result in streaking or spotting when the liquid dries.

It is also known to use sponge devices, impregnated with water or other cleaning solutions, to clean endoscopes. Several embodiments of such devices are shown in U.S. Pat. No. 5,274,874. The cleaning sponge may be used outside of the surgical area or may also be attached to the interior of an endoscopic trocar cannula so that the endoscope comes in contact with and is cleaned by a sponge device every time the endoscope is inserted into the trocar cannula. Such devices employing a sponge-type wiping element require the removal of the endoscope from its incision, and the surgical area as a whole, in order to provide effective cleaning. Endoscope removal may result in the loss of valuable time during endoscopic surgery. Further, additional entry and exit of the surgical area may be required when using these devices, resulting in additional trauma to the patient.

SUMMARY OF THE INVENTION

The invention is used while the endoscope is completely within a body cavity at the surgical area. Removal of the endoscope from the surgical area requires time and care beyond that necessary for the surgery, it may cause additional surgical trauma to the patient.

The retractable wipe of the invention includes a housing to contain the various parts of the device. A hollow tubular extension of the housing, which may be part of the same piece of material used to make the housing or may be a separate part, contains a retractable wiping element for the endoscope. The wiping element remains fully retracted within the tubular extension during its entry into an incision or orifice in the body, so that the wiping element does not become fouled during such entry. This provides a wiping element which is capable of effectively cleaning an endoscope. The end of the tubular extension is positioned at the tip of the endoscope. Once it is at the site of the optical endoscope lens, a manually actuated reciprocating mechanism can be selectively activated to extend the wiping element outward from the hollow tubular extension for wiping the lens tip of an endoscope. The wiping element can be retracted into its hollow tubular extension and the surgery may proceed with clear vision through the endoscope. The procedure may be repeated as necessary throughout the surgical process.

When inserted into an incision or orifice, especially one which does not contain the endoscope, the invention can be easily maneuvered to facilitate proper cleaning of an endoscope. The hollow tubular extension, which is thinner than the housing, extends out from the housing of the device so that the wiping device may be actuated without the bulk of the wiping element extending means being inserted into the incision or orifice. This minimizes the trauma caused by insertion of the invention.

While the endoscope is in place inside an incision or body orifice, the invention may be delivered to the endoscope in one of three ways. First, the invention may be inserted through an incision or orifice used for the entry of surgical instruments while surgical instruments are not in place in the incision/orifice. Second, it may be inserted through an incision or orifice used for the entry of surgical instruments while the surgical instruments are in place in the incision/orifice. Third, it may be inserted through an incision or body orifice that is used for the entry of the endoscope. The method of delivering the invention to the endoscope is dependent upon the type of surgery taking place. For example, the invention of the preferred embodiment is designed for use in ophthalmic endoscopic surgery. As such surgery permits only very small incisions to be made, the first method, inserting the invention in an incision used for surgical instruments while the instruments are not in place in the incision, is used.

The invention may alternately be built into or attached to an endoscope. A multichannel endoscope, as its name suggests, is a self-contained apparatus which has more than one channel. These multiple channels are placed into the body cavity simultaneously during endoscopic surgery. Use of a multi-channel endoscope requires only one incision or body orifice. One channel of the endoscope contains the visualization optics. Other channels, referred to as working channels, are used for the entry of surgical instruments. The retractable wipe of the invention may be placed into a working channel and operated from within this channel. Thus only one incision or body orifice is necessary to use the endoscope and the retractable wipe. In its other embodiments, one or more incisions or orifices are necessary to use both the endoscope and the retractable wipe.

The retractable wipe may be built in a variety of sizes. In that it may be very small, it is especially useful for ophthalmic endoscopic surgery. Due to the size and delicacy of the eye, ophthalmic surgery permits only very small incisions to be made for the surgical procedure. The retractable wipe may be constructed small enough to easily fit into such small incisions.

When made in a relatively large size, the retractable wipe is especially useful for laparoscopic surgery. Due to the abundance of fat and other bodily materials in the abdominal area, which tend to foul the endoscope, frequent endoscope cleaning is required to maintain a clear view of the surgical view. These materials have a tendency to cloud an endoscope almost immediately upon the entry of an endoscope into an incision. This tendency makes repeated cleaning an endoscope while it is located within the body imperative. The retractable wipe, in that it may be used within the body to clean an endoscope, is excellent for this purpose.

The retractable wipe is a relatively inexpensive, precision instrument. The wipe is disposable. It is intended to be used for one surgical procedure only, for the sake of preserving a sterile surgical environment. The retraction of the wipe element into the tubular extension provides a cleaning action as the edge of the tubular extension frictionally contacts the wipe element, squeezing and scraping the wipe element. However, if the wipe becomes fouled beyond the point of effective use, it may be disposed of and replaced during the surgical procedure.

Using the invention to clean an endoscope during surgery includes the following procedure:

At least one incision is made or a body orifice is used to permit an endoscope with visualization optics to enter into the body cavity and be positioned adjacent to the surgical field of interest. The working ends of surgical implements may be inserted separately or may be built into the endoscope, so that the surgery can be accomplished.

Alternately, additional incisions are made or additional orifices are utilized through which are positioned the working ends of various surgical implements such as cutting devices, etc. so that the surgery can be accomplished.

When the endoscope is inserted into and while it is located within a body cavity, it may become fouled with bodily fluids, blood, cartilage, muscle, etc. This prevents the endoscope from accomplishing its task of providing visualization of the surgical area.

The retractable wipe of the invention is inserted into the one of the incisions or orifices while the wiping element is in the retracted position to prevent the wiping element from being unnecessarily fouled or mangled.

Because the invention is placed into a body cavity while the endoscope is in a body cavity, the view from the endoscope may be used to properly guide the invention to the endoscope, assuming the endoscope is not completely fouled. Once properly emplaced adjacent to the tip of the endoscope, the wiping element is extended from within the hollow tubular extension and is wiped against the lens of the endoscope until the lens is sufficiently devoid of soiling matter to allow clear vision.

The wiping element is then retracted into the hollow tubular extension and the invention is then removed from the surgical area. This may entail a complete removal from the body cavity or merely moving the device aside within the cavity. The surgical process is then again ready to proceed. The procedure may be repeated as necessary throughout the surgical process.

Alternately, the retractable wipe may be built into or attached to the endoscope. The process for using the retractable wipe remains the same as it would otherwise, except that it need not be inserted into a body cavity and emplaced separate of the endoscope as it is already in the emplaced in the cavity in which the endoscope is located.

BRIEF DESCRIPTION OF THE DRAWINGS

FIG. 2 is a side view of the preferred embodiment with the wiping element in an extended position.

FIG. 3 is a top view of the preferred embodiment with the wiping element in an extended position.

FIG. 4 is a cross-sectional view, along line 1—1 of FIG. 3, with the wiping element in an extended position.

FIG. 5 is a cross-sectional view, along line 1—1 of FIG. 3, with the wiping element in a retracted position.

FIG. 6 is a cross-sectional view of an alternate embodiment with the wiping element in an extended position.

FIG. 7 is a cross-sectional view of an alternate embodiment with the wiping element in a retracted position.

FIG. 8 is a cross-sectional view of an another alternate embodiment with the wiping element in an extended position.

FIG. 9 is a cross-sectional view of an another alternate embodiment with the wiping element in a retracted position.

DESCRIPTION OF THE PREFERRED EMBODIMENT

Figure 1:
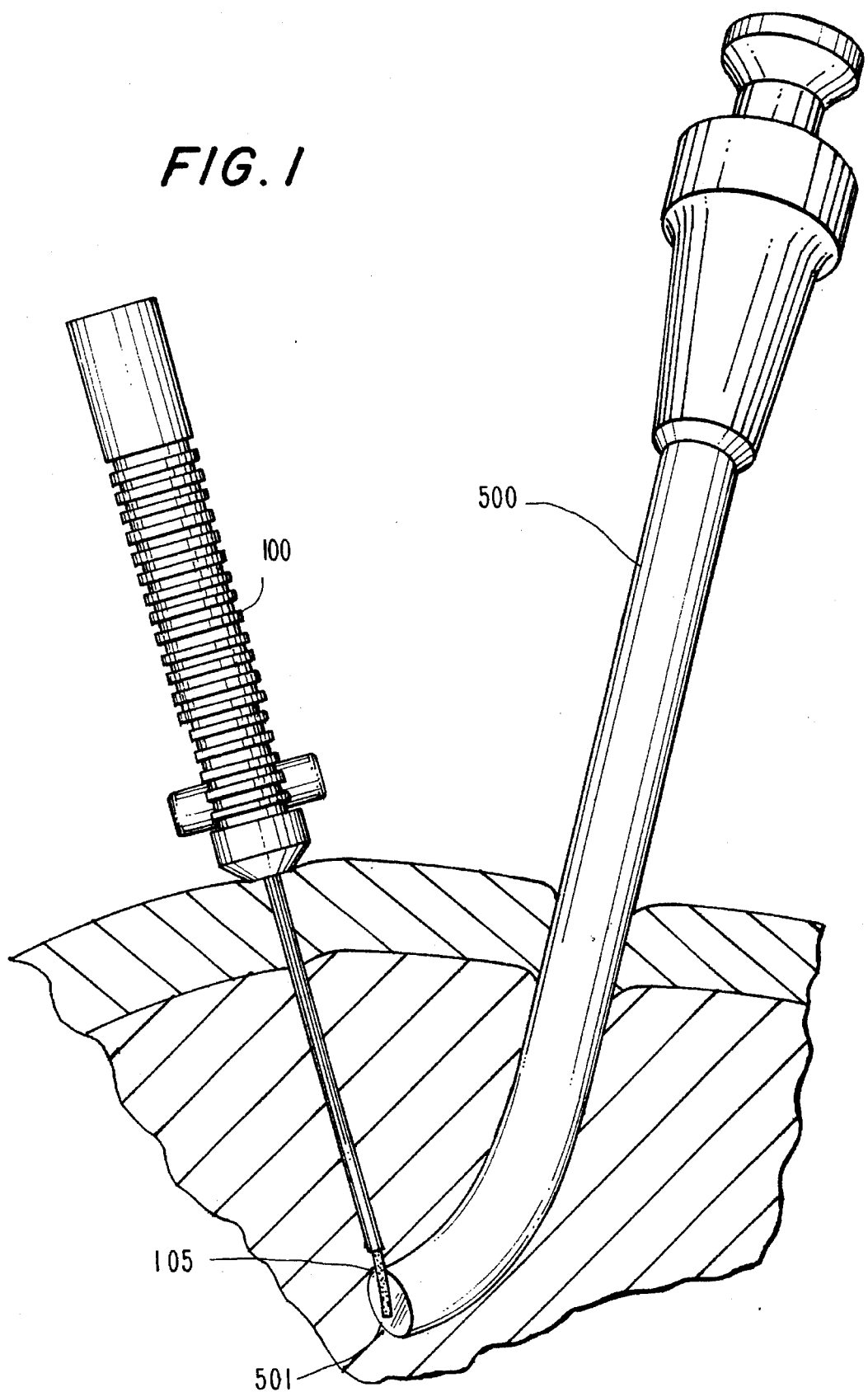
FIG. 1 typically shows the preferred embodiment in use during the endoscopic surgical procedure.

FIG. 1 shows the preferred embodiment of a retractable wipe device in use during the endoscopic surgical procedure. Endoscope 500 is located within an incision in the body cavity. Its visualization optics are located on endoscope tip 501. Retractable wipe assembly 100 is located in a second incision in the body cavity. Wiping element 105 is in an extended position. In this position wiping element 501 may engage and wipe endoscope tip 501 to clean it of soiling matter.

FIGS. 2–5 show the preferred embodiment, which is especially useful in ophthalmic endoscopic surgery. The retractable wipe assembly 100 includes a housing 101 which is preferably made a plastic material such as Delrin®. Housing 101 may be cylindrical in configuration and has a longitudinal cavity 111 along its length. Longitudinal cavity 111 is preferably comprised of two cavities of different diameters. A larger cavity 113 is adjacent to distal housing end 114 and a smaller cavity 115 is adjacent to proximal housing end 112. Using two different diameters allows the device to function by tightly containing tubular extension 102 in a smaller cavity while the larger cavity facilitates assembly of the device and also serves to conserve on materials used to make the device. Housing 101 preferably has a series of ridges 116 along its outer perimeter to facilitate manual grasping of the housing. Housing 101 has an aperture 110 cut through it. Aperture 110 is adjacent to proximal housing end 112. Aperture 110 has a proximal end 120 and a distal end 121. Smaller cavity 115 extends from proximal housing end 112 slightly beyond distal end 121 of aperture 110.

Tubular extension 102 has a hollow cavity running along its entire length. Tubular extension 102 is made of a thin gauge metal such as stainless steel. Tubular extension 102 extends from proximal end 120 of aperture 110, through smaller cavity 115, to a distance beyond proximal housing end 112. This distance may be varied depending upon the type of surgery the device is to be used in. The diameter of tubular extension 102 is dimensionally related to smaller cavity 115 to provide a tight and permanent mounting of tubular extension 102 within smaller cavity 115.

Needle 103 is made of a thin gauge metal such as stainless steel. Needle 103 is located within tubular extension 102 and is dimensionally related thereto to permit reciprocating movement within tubular extension 102 along the longitudinal axis 140 of tubular extension 102, which coincides with the longitudinal axis of housing 101.

Slide knob 104 is preferably made of the same material as housing 101, such as Delrin® plastic. Slide knob 104 is located within aperture 110. Needle 103 extends through slide knob 104 and is fixedly attached thereto. A distal portion 103-1 of needle 103 extends beyond both the slide knob 104 and distal aperture end 121 into the portion of longitudinal cavity 111 located immediately beyond distal aperture end 121. At least a portion of the cavity into which this distal portion 103-1 of needle 103 is located is of a lesser diameter than the remainder of larger cavity 113 to support distal portion 103-1 of needle 103 and maintain alignment of the needle between the retracted position and the extended position. The diameter of the portion of longitudinal cavity 111 may correspond to that of smaller cavity 115.

Wiping element 105 is made of a sponge material such as foam plastic. Wiping element 105 is located at proximal end 130 of needle 103 and has a diameter which is substantially similar to that of needle 103. Wiping element 105 is fixedly attached to needle 103 using an adhesive.

Slide knob 104 is selectively actuated to provide the extension and retraction of Wiping element 105. Referring to FIG. 4, when slide knob 104 is located at proximal aperture end 120, wiping element 105 is in an exposed, extended position to perform its wiping function while needle 103 remains within tubular extension 102. Referring to FIG. 5, when slide knob 104 is located at distal aperture end 121, wiping element 105 is in a completely retracted position within tubular extension 102.

The dimensions of the parts of the preferred embodiment for use in ophthalmic endoscopic surgery are as follows:

Housing 101 has a length, between proximal end 112 and proximal aperture end 120, of 0.250 inches. Smaller cavity 115 has a diameter of 0.034 inches.

Aperture 110 has a length, between proximal aperture end 120 and distal aperture end 121, of 0.375 inches and a width of 0.140 inches.

Tubular extension 102 has a length of 1.550 inches and a 0.034 inch diameter.

Needle 103 has a total length of 2.20 inches and a 0.022 inch diameter. Wipe element 105 has a length of 0.550 inches and a 0.022 inch diameter.

Slide knob 104 has a length of 0.500 inches, a diameter of 0.125 inches, and has an hole through its diameter. The hole has a 0.022 inch diameter.

In the alternate embodiment of FIGS. 6–7, larger cavity 113 contains an internal channel 201 along its circumference, near distal housing end 114. Screw mechanism 202 has a body 220 and a base member 221. Screw mechanism 202 has a proximal end 230 and a distal end 231. Base member 221 is located at distal end 231. Body 220 is hollow and contains internal threads 222 along its interior circumference at proximal end 230. Body 220 is located within larger cavity 113, at distal housing end 114, and is dimensionally related thereto to permit moving engagement within larger cavity 113. Body 220 has a ridge 223 running along its perimeter. Ridge 220 corresponds to and is dimensionally related to channel 201 such that it may rotationally move within channel 201, yet not fall out. This prevents screw mechanism 202 from falling out of larger cavity 113.

Connecting rod 103-2 is a rod extending through distal end 103-1 of needle 103. Connecting rod 103-2 is of a length dimensionally related to the interior diameter of body 220 such that rod 103-2 is movingly attached within threads 222 of body 220.

When screw mechanism 202 is turned clockwise within larger cavity 113, needle 103 is moved outward along the hollow cavity of tubular extension 102. This movement is due to rod 103-2 being driven along threads 222. This results in the extension of wiping element 105 from within tubular extension 102, as shown in FIG. 6. When screw mechanism 202 is turned counterclockwise within larger cavity 113, needle 103 is moved inward along the hollow cavity of tubular extension 102. This movement is due to rod 103-2 being driven along threads 222. This allows the retraction of wiping element 105 to within tubular extension 102, to the position shown in FIG. 7. Base member 221 is knurled to allow easy gripping and actuation of screw mechanism 202.

In FIG. 6, block 224 serves a stopping function to limit the extent of proximal movement. Block 224 is located within larger cavity 113, beyond distal end 231 of screw mechanism 202. Needle 103 goes through and is fixedly attached to block 224. When screw mechanism 202 is turned clockwise to extend the wipe, the extension process will be stopped when block 224 engages the distal end of large cavity 113. Accordingly at this stopped position, wiping element 105 will be fully extended while needle 103 remains within tubular extension 102. Thus, a stop means is provided.

Similarly, block 224 will prevent needle 103 from being retracted to the point of falling out of housing 101. In FIG. 7, when screw mechanism 202 is turned counterclockwise to retract the wipe, the retraction process will be stopped when block 224 engages body 220 at proximal end 230. Thus, needle 103 cannot fall out of screw mechanism 202 or housing 101.

Alternately, the extent of internal threads 222 may be used as a stopping means. The extent of internal threads 222 may be such that rod 103-2 will be stopped, by virtue of the end of the threading, when wiping element 105 is fully extended while needle 103 remains within tubular extension 102. Hence, a stop means is provided. The extent of internal threads 222 may also be such that rod 103-2 will be stopped when wiping element 105 is fully retracted. Thus, needle 103 cannot fall out of screw mechanism 202 or housing 101.

In the alternate embodiment of FIGS. 8–9, rod mechanism 301 includes a rod 302 located within larger cavity 113 and dimensionally related thereto to initiate reciprocating movement within larger cavity 113. Longitudinal cavity 111 has a protrusion 310 at distal end 114. Rod mechanism 301 has a groove 311 cut into a side. Groove 311 has a proximal end 320 and a distal end 321. Groove 311 surrounds and is adjacent to protrusion 310. Distal end 103-1 of needle 103 is fixedly attached to rod mechanism 301 at proximal end 340, Rod mechanism 301 has a detent at distal end 341 of the mechanism to facilitate easy, one finger actuation.

When rod mechanism 301 is actuated by being slid along larger cavity 113, needle 103 is slid along the hollow cavity of tubular extension 102. This facilitates the extension and retraction of wiping element 105 from within tubular extension 102. Referring to FIG. 9, when rod mechanism 301 is proximally slid so that proximal groove end 320 engages protrusion 310, wiping element 105 is in an exposed, extended position such that needle 103 remains within tubular extension 102. This engagement between proximal end 320 and protrusion 310 provides a stop means. Referring to FIG. 12, when rod mechanism 301 is distally slid so that distal groove end 321 engages protrusion 310, wiping element 105 is in a retracted position within tubular extension 102. This engagement between protrusion 310 and distal end 321 prevents rod mechanism 301 from sliding out of longitudinal cavity 111.

It should be noted that use of various other materials, various modifications in the configuration, and the other similar modifications and variations to which the invention is susceptible, may be practiced without departing from the scope, intent, and teaching of the claims.

I claim:

1. A retractable wipe for endoscopic surgical instruments comprising:
   A. a housing having manual gripping means about its external surface, distal and proximal ends, with a longitudinal cavity extending along at least a portion of its length and terminating at said proximal end;
   B. a hollow tubular extension projecting forward from said proximal end of said housing and communicating with said longitudinal cavity;
   C. a needle, extending along a longitudinal axis, located within said tubular extension, and dimensionally related thereto to permit reciprocating movement within said tubular extension along said longitudinal axis of said tubular extension and having a distal portion extending towards and beyond said distal end of said housing and a proximal end extending towards and beyond said proximal end of said housing;
   D. a wiping element at said proximal end of said needle; and
   E. a reciprocating means for selectively moving said needle along said axis of said tubular extension between a retracted position, in which said wiping element is within said tubular extension, and an extended position, in which said wiping element projects outward of said proximal end of said tubular extension.

2. The retractable wipe of claim 1 wherein said hollow tubular extension is a narrow member fixedly secured to said proximal end of said housing.

3. The retractable wipe of claim 1 wherein said longitudinal cavity of said housing is of two diameters, a smaller diameter at said proximal end of said housing and a larger diameter at said distal end of said housing.

4. The retractable wipe of claim 1 wherein said reciprocating means includes a knob projecting outward of said housing, said knob being operably connected to said needle and manually moveable between a first position, in which said wiping element is in said retracted position, and a second position, in which said wiping element is in said extended position.

5. The retractable wipe of claim 1 wherein said reciprocating means comprises a rod mechanism, having proximal and distal ends and being movingly located within said longitudinal cavity, said needle affixed at a distal end to said rod mechanism.

6. A retractable wipe for endoscopic surgical instruments comprising:
   A. a housing having distal and proximal ends, with a longitudinal cavity extending along at least a portion of its length and terminating at said proximal end;
   B. a hollow tubular extension projecting forward from said proximal end of said housing and communicating with said longitudinal cavity;
   C. a needle, extending along a longitudinal axis, located within said tubular extension, and dimensionally related thereto to permit reciprocating movement within said tubular extension said tubular extension along said longitudinal axis of said tubular extension and having a distal portion extending towards said distal end of said housing and a proximal end extending towards and beyond said proximal end of said housing;
   D. a wiping element at said proximal end of said needle;
   E. a reciprocating means for selectively moving said needle along said axis of said tubular extension between a retracted position, in which said wiping element is within said tubular extension, and an extended position, in which said wiping element projects outward of said proximal end of said tubular extension;
   F. said reciprocating means including a knob projecting outward of said housing, said knob being operably connected to said needle and manually moveable between a first position, in which said wiping element is in said retracted position, and a second position, in which said wiping element is in said extended position; and
   G. said housing includes an aperture to receive said knob, said knob including a portion located within said aperture and a manually operable portion extending outward of said aperture, said knob being moveable within said aperture to reciprocate said needle between said retracted position and said extended position.

7. The retractable wipe of claim 6 wherein said aperture includes distal and proximal ends, longitudinally spaced along said housing an amount equal to a longitudinal displacement between said retracted position and said extended position, said knob contacting said distal aperture end when said wiping element is in said retracted position and said knob contacting said proximal aperture end when said wiping element is in said extended position such that said ends provide stop means to limit said movement of said wiping element between said retracted position and said extended position.

8. The retractable wipe of claim 7 wherein said distal needle end is supported in a portion of said longitudinal cavity which extends from said distal aperture end towards said distal end of said housing.

9. A. a housing having distal and proximal ends, with a longitudinal cavity extending along at least a portion of its length and terminating at said proximal end;
   B. a hollow tubular extension projecting forward from said proximal end of said housing and communicating with said longitudinal cavity;
   C. a needle, extending along a longitudinal axis, located within said tubular extension, and dimensionally related thereto to permit reciprocating movement within said tubular extension said tubular extension along said longitudinal axis of said tubular extension and having a distal portion extending towards said distal end of said housing and a proximal end extending towards and beyond said proximal end of said housing;
   D. a wiping element at said proximal end of said needle;
   E. a reciprocating means for selectively moving said needle along said axis of said tubular extension between a retracted position, in which said wiping element is within said tubular extension, and an extended position, in which said wiping element projects outward of said proximal end of said tubular extension, F. said reciprocating means comprises a screw mechanism;

G. said screw mechanism having a body with proximal and distal ends, a base member at said distal end to facilitate rotation of said screw mechanism, and threading on a perimeter of the body of said screw mechanism, H. said longitudinal cavity having threads which correspond to the threads of the perimeter of the body of said screw mechanism;

I. said screw mechanism being located and threaded into within said longitudinal cavity at a distal end of said housing such that there is a moving engagement between them, and J. said needle being affixed to said proximal end of the body of said screw mechanism such that rotating said screw mechanism moves said needle through said hollow tubular extension.

10. The retractable wipe of claim 9 wherein said screw mechanism includes stop means to limit said extent of needle movement between said retracted position and said extended position.

11. The retractable wipe of claim 10 wherein the extent of said threaded moving engagement between said threads within said longitudinal cavity and said threads on said perimeter of the body of said screw mechanism provides said stop means.

12. The retractable wipe of claim 10 wherein said base member of said screw mechanism engages said housing to provide said stop means.

13. A. a housing having distal and proximal ends, with a longitudinal cavity extending along at least a portion of its length and terminating at said proximal end;

B. a hollow tubular extension projecting forward from said proximal end of said housing and communicating with said longitudinal cavity;

C. a needle, extending along a longitudinal axis, located within said tubular extension, and dimensionally related thereto to permit reciprocating movement within said tubular extension said tubular extension along said longitudinal axis of said tubular extension and having a distal portion extending towards said distal end of said housing and a proximal end extending towards and beyond said proximal end of said housing;

D. a wiping element at said proximal end of said needle;

E. a reciprocating means for selectively moving said needle along said axis of said tubular extension between a predetermined retracted position, in which said wiping element is within said tubular extension, and a predetermined extended position, in which said wiping element projects a predetermined distance outward of said proximal end of said tubular extension;

F. said reciprocating means comprises a rod mechanism, having proximal and distal ends and being movingly located within said longitudinal cavity, said needle affixed at a distal end to said rod mechanism; and G. said rod mechanism includes stop means at both of said retracted and extended positions to limit said extent of needle movement between said predetermined retracted position and said predetermined extended position.

14. The retractable wipe of claim 13 wherein said longitudinal cavity has a protrusion located adjacent to said distal end of said housing, said rod mechanism having a groove for containing said protrusion, the extent of said groove being within said distal or said proximal end of said rod mechanism such that said groove has ends to engage said protrusion, said protrusion and said groove engaging each other to provide said stop means.

15. A method of cleaning an endoscope lens while said endoscope is being used within a body cavity for endoscopic surgery comprising:

A. permitting an endoscope to enter into a body cavity and be positioned adjacent a surgical field;

B. allowing working ends of various surgical implements to be positioned in a body cavity adjacent said surgical field;

C. inserting a retractable wipe into at least one body cavity adjacent said surgical field while its wiping element is in a retracted position within a protective extension of said retractable wipe;

D. extending said wiping element from within a protective extension of said retractable wipe and wiping said wiping element against said endoscope lens until said lens is sufficiently devoid of soiling matter;

E. retracting said wiping element into said protective extension of said retractable wipe;

F. removing said retractable wipe from said immediate surgical field; and

G. repeating steps D, E, and F a desired number of times as said endoscopic lens becomes fouled with soiling matter during said surgery.

16. A method of cleaning an endoscope lens while said endoscope is being used within a body cavity for endoscopic surgery comprising said steps of:

A. permitting an endoscope, which has a retractable wipe attached thereto, to enter into a body cavity and be positioned adjacent a surgical field while its wiping element is in a retracted position within a protective extension of said retractable wipe;

B. allowing working ends of various surgical implements to be positioned in a body cavity adjacent said surgical field;

C. extending said wiping element from within a protective extension of said retractable wipe and wiping said wiping element against said endoscope lens until said lens is sufficiently devoid of soiling matter;

D. retracting said wiping element into said protective extension of said retractable wipe; and E. repeating steps C and D a desired number of times as said endoscopic lens becomes fouled with soiling matter during said surgery.

* * * * *